(12) United States Patent
Zappacosta et al.

(10) Patent No.: US 11,039,931 B2
(45) Date of Patent: Jun. 22, 2021

(54) INTERVERTEBRAL SPINAL IMPLANT

(71) Applicant: GLOBUS MEDICAL, INC., Audubon, PA (US)

(72) Inventors: Jason Zappacosta, Philadelphia, PA (US); Robert Ryan, Middletown, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 16/265,195

(22) Filed: Feb. 1, 2019

(65) Prior Publication Data
US 2020/0246160 A1    Aug. 6, 2020

(51) Int. Cl.
| A61F 2/44 | (2006.01) |
| A61F 2/46 | (2006.01) |
| A61F 2/28 | (2006.01) |
| A61F 2/30 | (2006.01) |
| A61B 17/86 | (2006.01) |

(52) U.S. Cl.
CPC .............. *A61F 2/4425* (2013.01); *A61F 2/28* (2013.01); *A61F 2/30771* (2013.01); *A61F 2/4455* (2013.01); *A61F 2/4611* (2013.01); *A61B 17/86* (2013.01); *A61F 2002/2835* (2013.01); *A61F 2002/30622* (2013.01); *A61F 2002/4629* (2013.01)

(58) Field of Classification Search
CPC .............................................. A61F 2/44–4465
See application file for complete search history.

(56) References Cited

U.S. PATENT DOCUMENTS

| | | |
|---|---|---|
| 5,370,692 A | 12/1994 | Fink et al. |
| 6,206,924 B1 | 3/2001 | Timm |
| 6,520,993 B2 | 2/2003 | James et al. |
| 6,520,996 B1 | 2/2003 | Manasas |
| 6,802,867 B2 | 10/2004 | Manasas |
| 7,238,203 B2 | 7/2007 | Bagga et al. |
| 7,537,664 B2 | 5/2009 | O'Neill et al. |
| 7,892,239 B2 | 2/2011 | Warnick et al. |
| 7,918,891 B1 | 4/2011 | Curran et al. |
| 7,959,675 B2 | 6/2011 | Gately |
| 7,976,549 B2 | 7/2011 | Dye et al. |
| 8,012,156 B2 * | 9/2011 | Marquez Alvarez ........ A61F 2/4611 606/86 A |
| 8,147,554 B2 | 4/2012 | Hansell et al. |
| D665,081 S | 8/2012 | Hansell et al. |
| 8,377,139 B2 | 2/2013 | Laubert et al. |
| 8,425,607 B2 | 4/2013 | Waugh et al. |
| 8,430,930 B2 | 4/2013 | Hunt |
| 8,506,629 B2 | 8/2013 | Weiland |
| 8,530,560 B2 | 9/2013 | Kerr et al. |
| 8,545,566 B2 | 10/2013 | Niemiec et al. |
| 8,551,173 B2 | 10/2013 | Lechmann et al. |
| 8,603,175 B2 * | 12/2013 | Thibodeau ............ A61F 2/4465 623/17.16 |
| D700,332 S | 2/2014 | Tyber |

(Continued)

Primary Examiner — Eduardo C Robert
Assistant Examiner — Michelle C Eckman

(57) ABSTRACT

An intervertebral implant for implantation in an intervertebral space between vertebrae. The implant includes a body, an articulating element, and a blocking member. The articulating element can articulate in-situ, thereby allowing articulation of the spinal implant into a desired position within the disc space.

20 Claims, 9 Drawing Sheets

(56) References Cited

U.S. PATENT DOCUMENTS

| | | | |
|---|---|---|---|
| 8,728,387 B2 | 5/2014 | Jones et al. | |
| 8,735,773 B2 | 5/2014 | Lang | |
| 8,843,229 B2 | 9/2014 | Vanasse et al. | |
| 8,858,637 B2* | 10/2014 | Milz | A61F 2/442 623/17.16 |
| 8,900,311 B2 | 12/2014 | Ciupik et al. | |
| 8,932,356 B2 | 1/2015 | Kraus | |
| 8,992,703 B2 | 3/2015 | O'Neill et al. | |
| 8,998,924 B2* | 4/2015 | Simpson | A61F 2/4611 606/105 |
| 9,005,294 B2 | 4/2015 | You et al. | |
| 9,034,048 B2 | 5/2015 | Choren | |
| 9,101,487 B2 | 8/2015 | Petersheim | |
| 9,138,330 B2 | 9/2015 | Hansell et al. | |
| 9,186,257 B2 | 11/2015 | Geisler et al. | |
| 9,220,542 B2* | 12/2015 | Kerboul | A61B 17/808 |
| 9,220,607 B2* | 12/2015 | Palmatier | A61F 2/442 |
| 9,259,327 B2 | 2/2016 | Niemiec et al. | |
| 9,271,845 B2 | 3/2016 | Hunt et al. | |
| 9,283,091 B2 | 3/2016 | Melkent et al. | |
| 9,295,562 B2 | 3/2016 | Lechmann et al. | |
| 9,364,896 B2 | 6/2016 | Christensen et al. | |
| 9,421,108 B2 | 8/2016 | Hunt | |
| 9,433,510 B2 | 9/2016 | Lechmann et al. | |
| 9,451,940 B2* | 9/2016 | Spann | A61F 2/447 |
| 9,456,901 B2 | 10/2016 | Jones et al. | |
| 9,486,326 B2 | 11/2016 | Gahman et al. | |
| 9,492,286 B2 | 11/2016 | Biedermann et al. | |
| 9,545,317 B2 | 1/2017 | Hunt | |
| 9,549,823 B2 | 1/2017 | Hunt et al. | |
| 9,572,669 B2 | 2/2017 | Hunt et al. | |
| 9,636,226 B2 | 5/2017 | Hunt | |
| 9,642,722 B2 | 5/2017 | Baynham | |
| 9,649,200 B2 | 5/2017 | Wickham | |
| 9,662,157 B2 | 5/2017 | Schneider et al. | |
| 9,662,226 B2 | 5/2017 | Wickham | |
| 9,700,428 B2 | 7/2017 | Niemiec et al. | |
| 9,730,806 B2 | 8/2017 | Capote | |
| D797,934 S | 9/2017 | Pimenta et al. | |
| 9,757,235 B2 | 9/2017 | Hunt et al. | |
| 9,775,711 B2 | 10/2017 | Li et al. | |
| 9,782,269 B2 | 10/2017 | Hansell et al. | |
| 9,782,270 B2 | 10/2017 | Wickham | |
| 9,788,972 B2 | 10/2017 | Flickinger et al. | |
| 9,801,731 B2 | 10/2017 | Sawyer et al. | |
| 9,895,235 B2 | 2/2018 | Melkent et al. | |
| 9,907,657 B2 | 3/2018 | Fonte et al. | |
| 9,931,224 B2 | 4/2018 | Lindenmann et al. | |
| 10,034,761 B2 | 7/2018 | Baccelli et al. | |
| 10,130,490 B2 | 11/2018 | Hansell et al. | |
| 10,342,677 B2* | 7/2019 | Ries | A61B 17/1757 |
| 10,478,313 B1* | 11/2019 | Sweeney, III | A61F 2/4611 |
| 2005/0096745 A1* | 5/2005 | Andre | A61F 2/4611 623/17.11 |
| 2006/0229627 A1* | 10/2006 | Hunt | A61B 17/1659 606/86 R |
| 2007/0142843 A1* | 6/2007 | Dye | A61F 2/4611 606/99 |
| 2007/0213737 A1* | 9/2007 | Schermerhorn | A61F 2/4611 606/86 R |
| 2007/0213826 A1* | 9/2007 | Smith | A61F 2/4465 623/17.11 |
| 2007/0225726 A1* | 9/2007 | Dye | A61F 2/4465 606/99 |
| 2007/0225808 A1* | 9/2007 | Warnick | A61F 2/4611 623/17.11 |
| 2008/0009880 A1* | 1/2008 | Warnick | A61F 2/4455 606/99 |
| 2008/0027544 A1* | 1/2008 | Melkent | A61F 2/442 623/17.11 |
| 2008/0065082 A1* | 3/2008 | Chang | A61B 17/1659 606/85 |
| 2008/0077153 A1* | 3/2008 | Pernsteiner | A61F 2/4425 606/99 |
| 2008/0077241 A1* | 3/2008 | Nguyen | A61B 17/1659 623/17.11 |
| 2008/0091211 A1* | 4/2008 | Gately | A61F 2/4465 606/99 |
| 2008/0140085 A1* | 6/2008 | Gately | A61F 2/4465 606/99 |
| 2008/0161927 A1* | 7/2008 | Savage | A61L 27/18 623/17.16 |
| 2008/0221694 A1* | 9/2008 | Warnick | A61F 2/4465 623/17.16 |
| 2008/0306488 A1* | 12/2008 | Altarac | A61F 2/4611 606/99 |
| 2008/0306489 A1* | 12/2008 | Altarac | A61F 2/4611 606/99 |
| 2008/0306557 A1* | 12/2008 | Altarac | A61F 2/4611 606/86 A |
| 2009/0234364 A1* | 9/2009 | Crook | A61F 2/4611 606/99 |
| 2009/0276049 A1* | 11/2009 | Weiland | A61F 2/4611 623/17.16 |
| 2010/0094422 A1* | 4/2010 | Hansell | A61F 2/4465 623/17.16 |
| 2010/0191337 A1* | 7/2010 | Zamani | A61F 2/4611 623/17.16 |
| 2010/0256759 A1* | 10/2010 | Hansell | A61F 2/4465 623/17.11 |
| 2010/0256760 A1* | 10/2010 | Hansell | A61F 2/4611 623/17.11 |
| 2011/0106259 A1* | 5/2011 | Lindenmann | A61F 2/4611 623/17.16 |
| 2011/0166654 A1* | 7/2011 | Gately | A61F 2/4465 623/17.11 |
| 2011/0264218 A1* | 10/2011 | Asaad | A61F 2/4465 623/17.16 |
| 2011/0276142 A1* | 11/2011 | Niemiec | A61F 2/30771 623/17.16 |
| 2011/0319998 A1* | 12/2011 | O'Neil | A61F 2/4455 623/17.16 |
| 2012/0158143 A1 | 6/2012 | Shapiro | |
| 2012/0165943 A1* | 6/2012 | Mangione | A61F 2/4465 623/17.16 |
| 2012/0185045 A1* | 7/2012 | Morris | A61F 2/442 623/17.11 |
| 2012/0209383 A1* | 8/2012 | Tsuang | A61F 2/4465 623/17.12 |
| 2012/0277869 A1* | 11/2012 | Siccardi | A61F 2/4465 623/17.16 |
| 2012/0292814 A1 | 11/2012 | Spratt et al. | |
| 2013/0006362 A1* | 1/2013 | Biedermann | A61F 2/44 623/17.16 |
| 2013/0023937 A1* | 1/2013 | Biedermann | A61F 2/4465 606/279 |
| 2013/0103102 A1* | 4/2013 | Taylor | A61F 2/4465 606/86 A |
| 2013/0116793 A1 | 5/2013 | Kloss | |
| 2013/0268077 A1* | 10/2013 | You | A61F 2/4455 623/17.16 |
| 2014/0018815 A1* | 1/2014 | Kirschman | A61F 2/4465 606/99 |
| 2014/0039626 A1* | 2/2014 | Mitchell | A61F 2/4611 623/17.16 |
| 2014/0058512 A1* | 2/2014 | Petersheim | A61F 2/4611 623/17.16 |
| 2014/0058513 A1* | 2/2014 | Gahman | A61F 2/4611 623/17.16 |
| 2014/0172105 A1* | 6/2014 | Frasier | A61F 2/442 623/17.16 |
| 2014/0249628 A1* | 9/2014 | Weiman | A61F 2/442 623/17.15 |
| 2014/0249630 A1* | 9/2014 | Weiman | A61F 2/442 623/17.16 |
| 2014/0249631 A1* | 9/2014 | Weiman | A61F 2/442 623/17.16 |
| 2014/0249632 A1* | 9/2014 | Weiman | A61F 2/4425 623/17.16 |

(56) References Cited

U.S. PATENT DOCUMENTS

| | | | | |
|---|---|---|---|---|
| 2015/0012099 | A1* | 1/2015 | Baccelli | A61F 2/4611 623/17.16 |
| 2015/0018956 | A1 | 1/2015 | Steinmann et al. | |
| 2015/0045892 | A1 | 2/2015 | Lynn et al. | |
| 2015/0100126 | A1* | 4/2015 | Melkent | A61F 2/4455 623/17.16 |
| 2015/0134063 | A1 | 5/2015 | Steinmann et al. | |
| 2015/0257891 | A1* | 9/2015 | Puno | A61F 2/4684 623/17.16 |
| 2016/0045333 | A1* | 2/2016 | Baynham | A61F 2/442 623/17.16 |
| 2016/0051371 | A1 | 2/2016 | DeFelice et al. | |
| 2016/0095718 | A1* | 4/2016 | Burkhardt | A61F 2/4455 623/17.16 |
| 2016/0113776 | A1* | 4/2016 | Capote | A61F 2/447 623/17.15 |
| 2016/0199193 | A1 | 7/2016 | Willis et al. | |
| 2016/0213485 | A1 | 7/2016 | Shaufler et al. | |
| 2016/0213486 | A1 | 7/2016 | Nunley et al. | |
| 2016/0213487 | A1 | 7/2016 | Wilson et al. | |
| 2016/0262908 | A1 | 9/2016 | Arramon et al. | |
| 2016/0270920 | A1 | 9/2016 | Dawson et al. | |
| 2016/0317323 | A1* | 11/2016 | Cho | A61F 2/4611 |
| 2016/0317324 | A1* | 11/2016 | Cho | A61F 2/4611 |
| 2016/0324656 | A1 | 11/2016 | Morris et al. | |
| 2017/0014240 | A1* | 1/2017 | Seifert | A61F 2/4455 |
| 2017/0014244 | A1* | 1/2017 | Seifert | A61F 2/447 |
| 2017/0020570 | A1 | 1/2017 | Petersheim | |
| 2017/0020685 | A1 | 1/2017 | Geisler et al. | |
| 2017/0042697 | A1 | 2/2017 | McShane, III et al. | |
| 2017/0056194 | A1* | 3/2017 | Biedermann | A61F 2/4465 |
| 2017/0112635 | A1* | 4/2017 | Ty | A61F 2/4611 |
| 2017/0156880 | A1 | 6/2017 | Halverson et al. | |
| 2017/0165082 | A1* | 6/2017 | Faulhaber | A61F 2/4455 |
| 2017/0172757 | A1* | 6/2017 | Melkent | A61F 2/4611 |
| 2017/0172758 | A1 | 6/2017 | Field et al. | |
| 2017/0172759 | A1* | 6/2017 | Kukkar | A61F 2/4465 |
| 2017/0182222 | A1 | 6/2017 | Paddock et al. | |
| 2017/0209286 | A1* | 7/2017 | Palmatier | A61F 2/44 |
| 2017/0216035 | A1 | 8/2017 | Hunt | |
| 2017/0216036 | A1 | 8/2017 | Cordaro | |
| 2017/0239064 | A1 | 8/2017 | Cordaro | |
| 2017/0258606 | A1 | 9/2017 | Afzal | |
| 2017/0266016 | A1* | 9/2017 | Faulhaber | A61F 2/4611 |
| 2017/0290679 | A1 | 10/2017 | Niemiec et al. | |
| 2017/0296352 | A1 | 10/2017 | Richerme et al. | |
| 2017/0325966 | A1* | 11/2017 | Capote | A61F 2/447 |
| 2017/0333205 | A1 | 11/2017 | Joly et al. | |
| 2017/0340453 | A1 | 11/2017 | Kaufmann et al. | |
| 2017/0354513 | A1 | 12/2017 | Maglaras et al. | |
| 2017/0360563 | A1 | 12/2017 | Hunt et al. | |
| 2017/0360574 | A1* | 12/2017 | Hansell | A61B 90/39 |
| 2018/0014938 | A1 | 1/2018 | Hagen et al. | |
| 2018/0021149 | A1* | 1/2018 | Boehm | A61F 2/4611 606/99 |
| 2018/0042732 | A1* | 2/2018 | Seifert | A61F 2/30771 |
| 2018/0085233 | A1* | 3/2018 | Palmatier | A61F 2/4611 |
| 2018/0092754 | A1* | 4/2018 | Jang | A61F 2/4455 |
| 2018/0256363 | A1* | 9/2018 | Moon | A61F 2/4455 |
| 2018/0289506 | A1* | 10/2018 | Kim | A61L 27/18 |
| 2018/0303624 | A1* | 10/2018 | Shoshtaev | A61F 2/4611 |
| 2018/0333272 | A1* | 11/2018 | Mirda | A61F 2/447 |
| 2018/0360621 | A1* | 12/2018 | Moon | A61F 2/442 |
| 2019/0328545 | A1* | 10/2019 | Siccardi | A61F 2/4465 |
| 2019/0328546 | A1* | 10/2019 | Palagi | A61F 2/4611 |
| 2019/0374350 | A1* | 12/2019 | Milz | B25B 23/1427 |
| 2019/0380843 | A1* | 12/2019 | Kim | A61F 2/4611 |

* cited by examiner

INTERVERTEBRAL SPINAL IMPLANT

FIELD

The present application generally relates to intervertebral spacers, and in particular, to articulating intervertebral spacers.

BACKGROUND

The vertebrate spine is the axis of the skeleton providing structural support for the other parts of the body. Adjacent vertebrae of the spine are supported by an intervertebral disc, which serves as a mechanical cushion permitting controlled motion between vertebral segments of the axial skeleton.

The spinal disc can be displaced or damaged due to trauma, disease, degenerative defects or wear over an extended period of time. To alleviate back pain caused by disc herniation or degeneration, the disc can be removed and replaced by an implant that promotes fusion of the remaining bone anatomy. The implant, such as a spacer or cage body, should be sufficiently strong to support the spine under a wide range of loading conditions. There remains a need for improved implants that facilitate intervertebral fusion and serve as a means to restore intervertebral height and/or lordosis.

SUMMARY

To meet this and other needs, intervertebral implants, systems, and methods are provided. The implant may feature a pivoting mechanism housed within the spacer. The pivoting mechanism allows for the implant to be inserted into in the disc space in a first, initial position and then subsequently pivoted into a second, final position. The ability to articulate the implant in-situ allows the surgeon to safely navigate past the posterior neural elements and/or optimize the implant placement relative to the patient anatomy.

The implant may also feature a central lumen to house bone graft material. It is through this central lumen where most of the fusion may occur. The implants of the disclosure incorporate a volumetric, interconnected porosity throughout the entire spacer. This enables bone to grow into and/or through the spacer, making it part of the fusion mass. The incorporation of a volumetric, interconnected porosity within the implant may encourage faster, stronger intervertebral fusion.

The implant may be constructed by typical manufacturing processes (e.g., manufactured from a titanium alloy) or may be constructed by additive manufacturing, such as 3D printing. The additive manufacturing may incorporate a volumetric, interconnected porosity through the entire spacer or a portion thereof. The porosity may enable bone growth into the spacer, thereby making it part of the fusion mass and encouraging a faster and/or stronger fusion.

According to one embodiment, an intervertebral implant for implantation in an intervertebral space between vertebrae is disclosed. The implant includes an implant body, a pivoting member, and a blocking member. The implant body extends from an upper surface to a lower surface. The implant body has a front end, a rear end and a pair of spaced apart first and second side walls extending between the front and rear ends such that an interior chamber is defined within. The rear end includes an elongated opening defining at least one track and a dimple. The pivoting member includes an enlarged head portion and an elongated shaft portion terminating at a distal end. The distal end of the pivoting member is positioned within the dimple and the enlarged head portion is positioned within the at least one track. The blocking member extends from the upper surface to the lower surface of the implant body and secures the pivoting member within the at least one track. The pivoting member is configured to slide along the at least one track and articulate from an initial position to a final position. The dimple may act as a pivot point for the pivoting member, and the at least one track may extend along an arc having a constant radius from the pivot point.

According to another embodiment, a method of forming an intervertebral implant for implantation in an intervertebral space between vertebrae is provided. The method includes utilizing a 3D printing process to deposit individual layers. The layers may contain solid and porous portions, which ultimately define the overall shape and design of the device. The at least one track may be further finished using a dovetail cutter having a curved cutting surface configured to form a smooth vertical region for the at least one track.

According to yet another embodiment, a method of assembling the implant may include aligning the distal tip of the pivoting member a gap in the at least one track along an axis. The pivoting member is seated within the implant, but is not yet engaged with the at least one track. The pivoting member is articulated into a neutral position, into alignment with the at least one track, and exposing an opening to receive the blocking member. The blocking member is installed in the opening, thereby preventing the blocking member from being removed from the implant body. Once installed, the pivoting member may articulate, in-situ, along the at least one track into the final, implanted position.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION

Embodiments of the disclosure are generally directed to intervertebral implants, systems, and method of use thereof. The implants can be used to fuse together a treated area of the spine while restoring and/or maintaining the proper spacing and natural curvature of the spine. The treated area can include regions between adjacent vertebral bodies so that the height of the implant corresponds approximately to the height of the disc. The implants described herein may be configured to articulate with ease into a desired position in between the two vertebrae.

Figure 1:
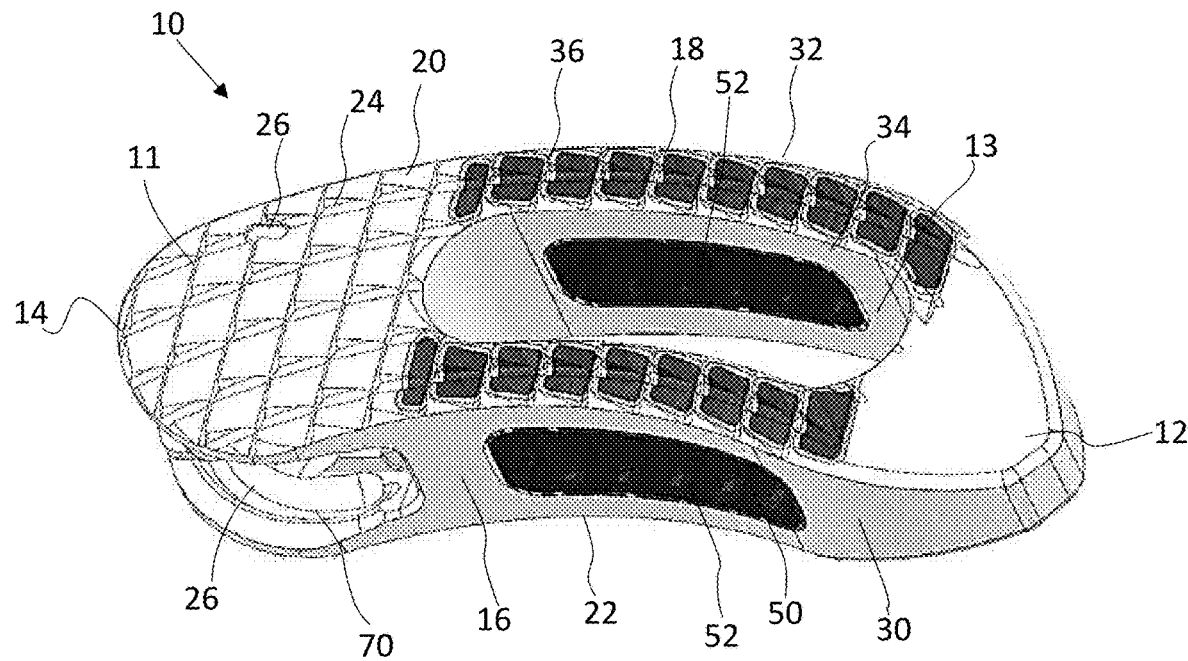
FIG. 1 is a perspective view of an implant according to one embodiment.
Figure 2:
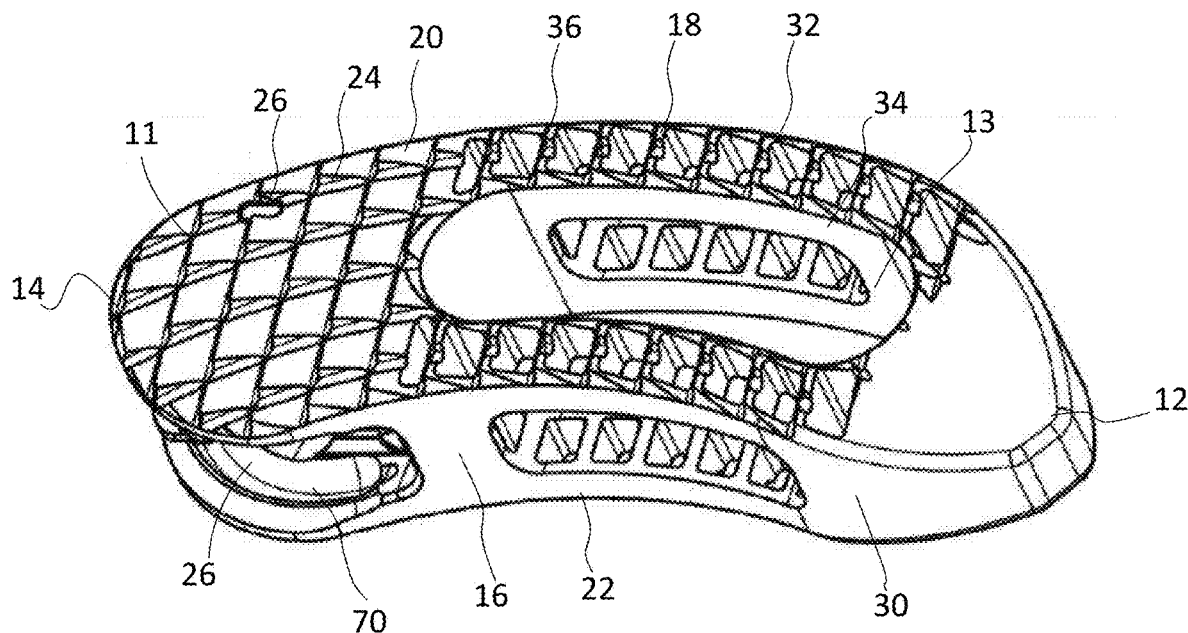
FIG. 2 is a perspective view of the implant shown in FIG. 1 with the porous portions omitted for clarity.
Figure 3:
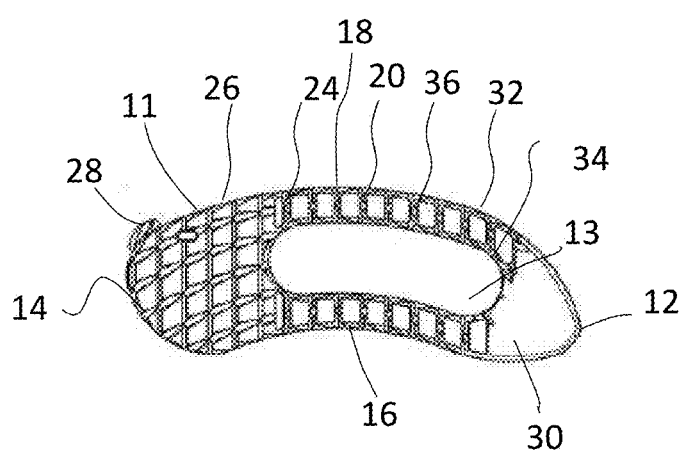
FIG. 3 is a top down view of the implant of FIG. 1 with the porous portions omitted.
Figure 4:
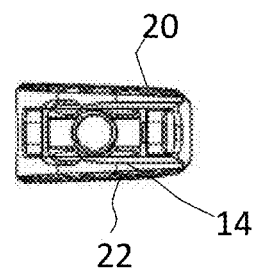
FIG. 4 is a back view of the implant of FIG. 3.
Figure 5:
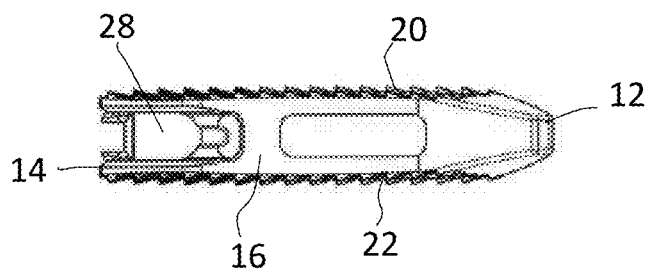
FIG. 5 is a side view of the implant of FIG. 3.
Figure 6:
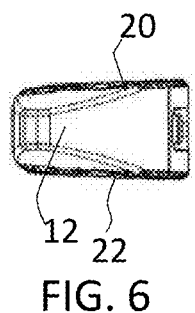
FIG. 6 is a front view of the implant of FIG. 3.

Referring now to FIG. 1, one embodiment of a transforaminal lumbar interbody fusion (TLIF) implant assembly 10 will be described. As illustrated, the implant 10 has a body 11 in the form of a generally banana-style cage. The body 11 is defined by a tapered front end 12, a rear end 14 and side walls 16 and 18 extending therebetween. In particular, side walls 16 and 18 may be curved, such that side wall 16 is concave and side wall 18 is convex. The front end 12 may be tapered to ease insertion into the disc space, and rear end 14 may be convexly curved. A hollow interior chamber 13 may be defined within the body 11. The hollow interior chamber 13 may be configured to receive bone growth promoting materials, for example, such as autogenous and/or allograft bone. The implant 10 has an upper surface 20 and a lower surface 22. The upper and lower surfaces 20, 22 may be substantially parallel or otherwise configured to provide the proper intervertebral spacing. The upper and lower surfaces 20, 22 may define a plurality of teeth, ridges, or serrations 24. In some embodiments, the serrations 24 may be defined only by the solid support structure (e.g., near the rear end 14) or by both the solid support structure 30 and the porous structure 50 (e.g., in a central region of the implant 10). The serrations 24 may be configured to provide migration resistance of the implant 10. The leading, front end may be smooth, tapered, and free of teeth or serrations.

Figure 7:
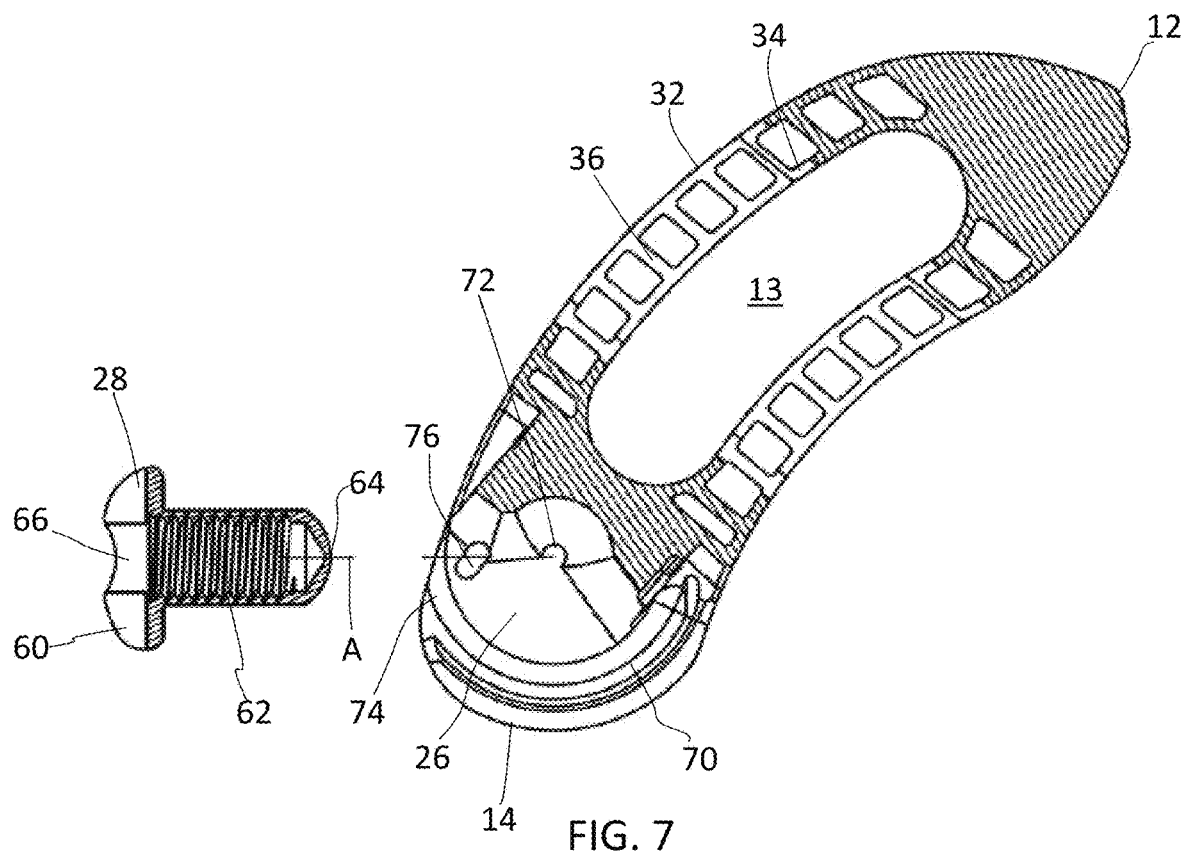
FIG. 7 is an exploded view of an implant with the porous portions omitted and the pivoting member when the pivoting member is aligned with the gap in the track.

The rear end 14 of the implant 10 includes an elongated opening 26 between the upper and lower surfaces 20, 22 for receiving a pivoting member 28. The elongated opening 26 ma curved to follow the outer contour of the convexly curved rear end 14. As best seen in FIG. 7, the pivoting member 28 includes an enlarged head portion 60 and an elongated shaft portion 62 extending therefrom. The elongated shaft portion 62 may terminate at a distal end 64, which may be rounded, pointed, or otherwise configured. The distal end 64 may be configured to be received within a female dimple 72 within the opening 26, which acts as a pivot point for the pivoting member 28. The exterior shaft portion 62 of the pivoting member 28 may be non-threaded and smooth or otherwise configured. The head portion 60 of the pivoting member 28 may include an instrument receiving recess 66 and the instrument receiving recess 66 may extend into the shaft portion 62 of the pivoting member 28, thereby forming a blind hole. In one embodiment, the portion of the receiving recess 66 extending into the shaft portion 62 of the pivoting member 28 may be internally threaded, for example, to engage an externally threaded instrument (not shown). The head portion 60 of the pivoting member 28 may be rounded, contoured, notched, or otherwise configured to be received within track or tracks 70 defined in the opening 26.

The elongate opening 26 within the rear end 14 of the implant 10 may extend a depth into the implant 10 to form a blind recess. The elongated opening 26 may further define one or more tracks 70. The track 70 may define a female recess having a length greater than its width. The track 70 may be curved to mimic the outer surface of the implant 10. The one or more tracks 70 may be positioned proximate to the upper and/or lower surfaces 20, 22 of the implant 10. In an exemplary embodiment, the elongated opening 26 contains a first track near the upper surface 20 and a second track near the lower surface 22 such that an upper portion of the head portion 60 of the pivoting member 28 is received in the first track 70 and a lower portion of the head portion 60 of the pivoting member 28 is received in the second track 70. The elongated opening 26 may further define one or more pivoting dimples 72. The pivoting dimple 72 may define a female indentation within the body 11 of the implant 10. The pivoting dimple 72 may be centrally located within the implant 10. The distal end 64 of the pivoting member 28 may be receivable within the dimple 72, which acts as a pivot point for the pivoting member 28. The track or tracks 70 may extend along an arc having a constant radius from the pivot point.

The implant 10 may further include a blocking member 80. A through-opening 76 may extend from the upper surface 20 to the lower surface 22 of the implant 10 or a portion thereof. The blocking member 80 may have an elongated body and is receivable within opening 76, for example, from the upper surface 20 to the lower surface 22 to secure the pivoting member 28 within the elongated opening 26 and within the track or tracks 70. The blocking member 80 may be secured in opening 76 via an interference fit or friction fit or otherwise secured in the opening 76.

Figure 8:
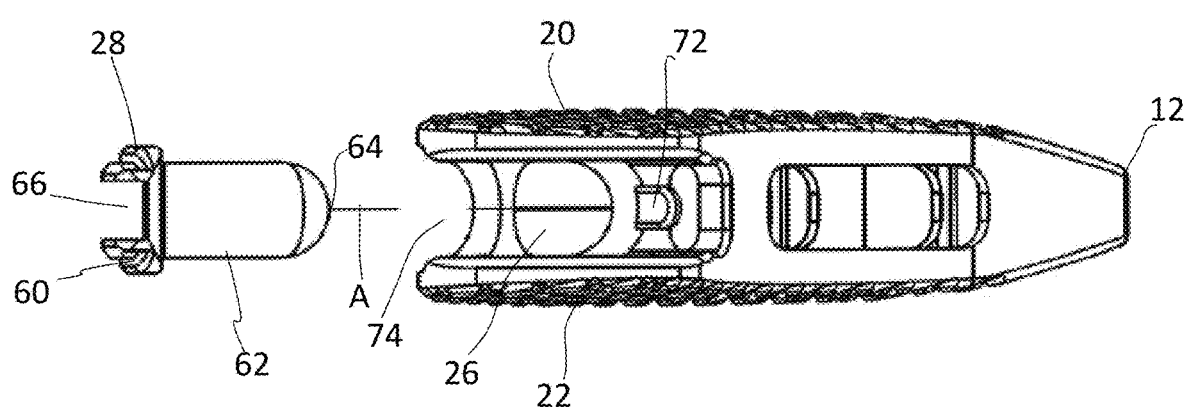
FIG. 8 is an exploded rear view of FIG. 7 when the pivoting member is aligned with the gap in the track.
Figure 9:
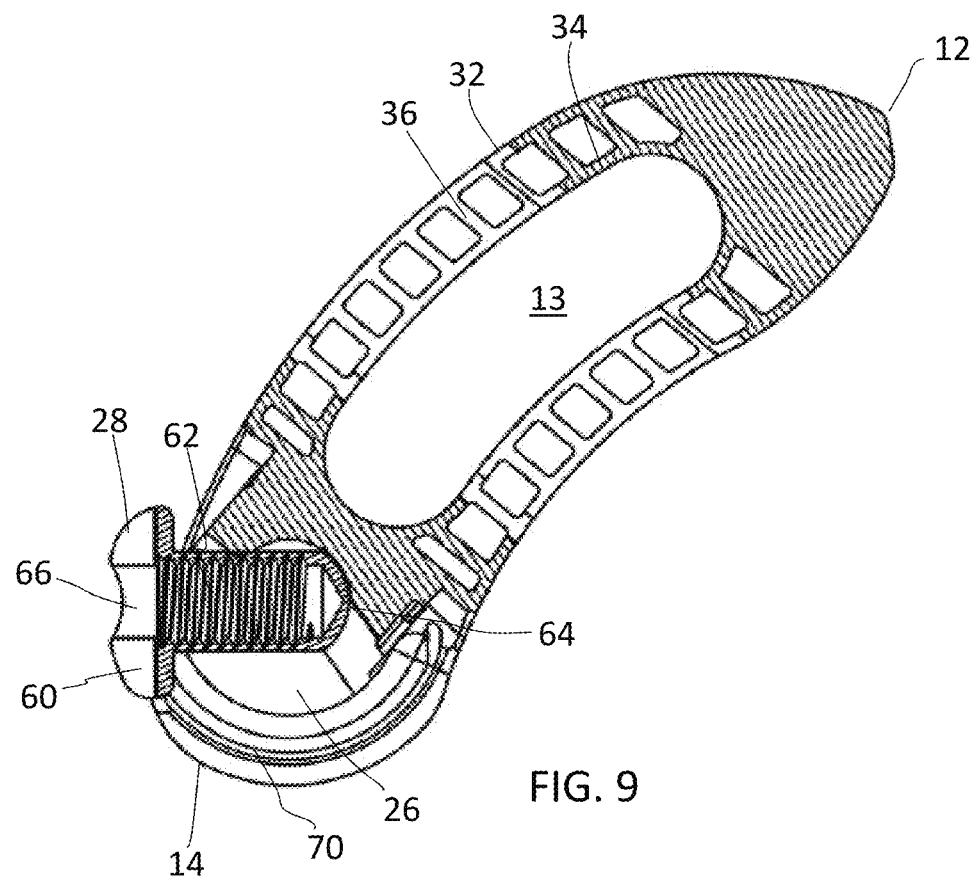
FIG. 9 is an assembled view of the implant with the porous portions omitted and the pivoting member when the pivoting member is seated within the spacer but not yet engaged to the track.
Figure 10:
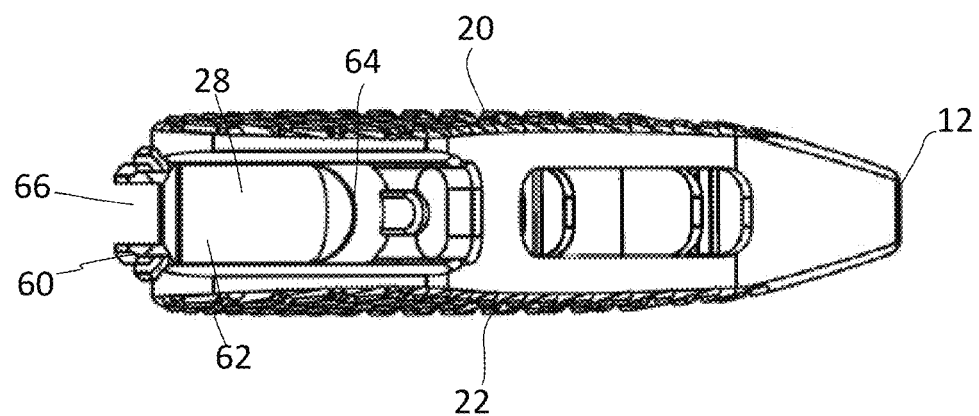
FIG. 10 is an assembled rear view of FIG. 9 when the pivoting member is seated within the spacer but not yet engaged to the track.
Figure 11:
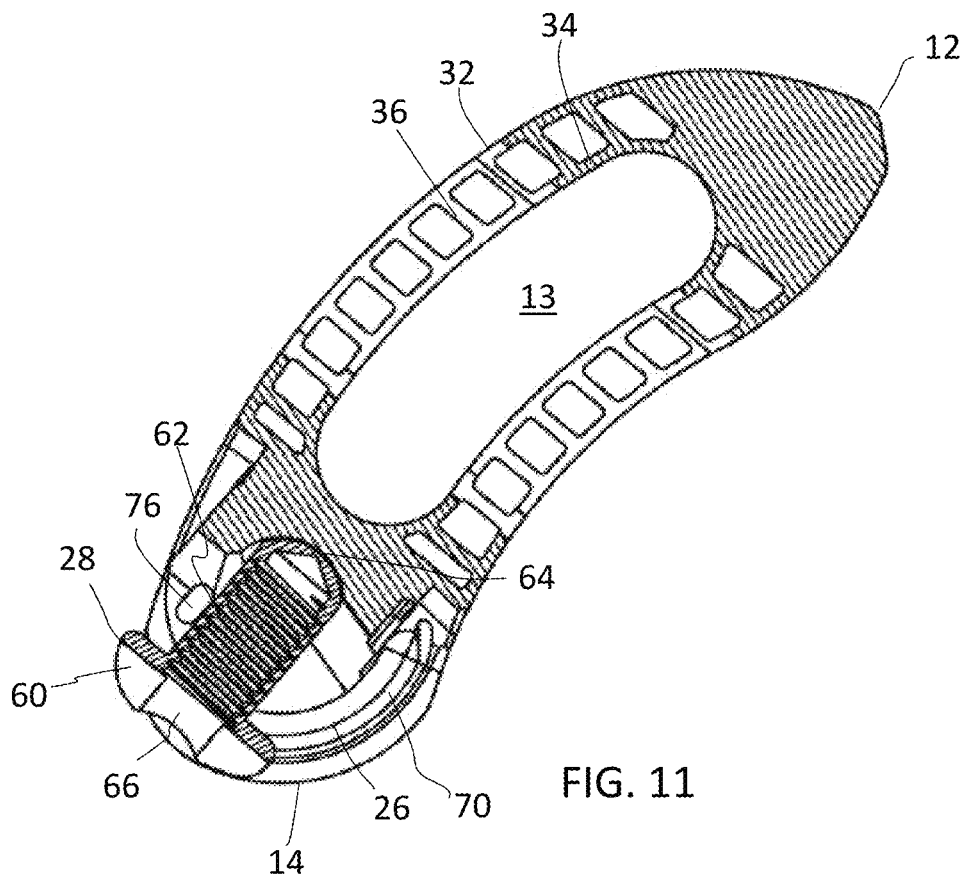
FIG. 11 is an assembled view of the implant with the porous portions omitted and the pivoting member when the pivoting member is articulated in a neutral position.
Figure 12:
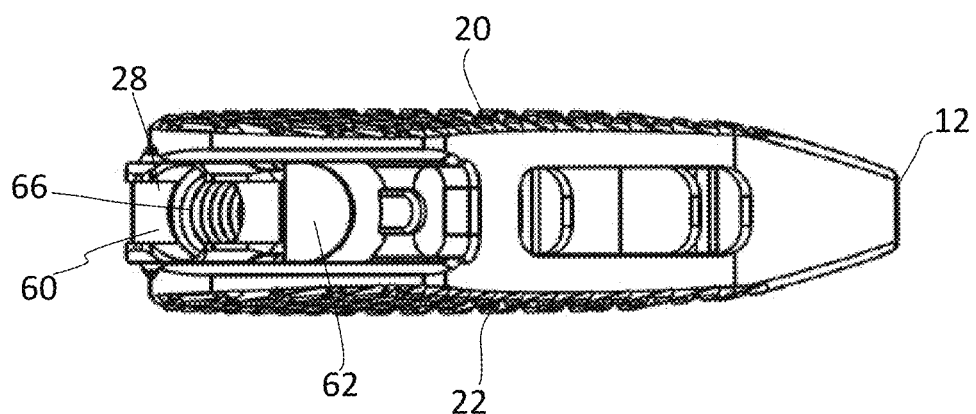
FIG. 12 is an assembled rear view of FIG. 11 when the pivoting member is articulated into the neutral position.

Referring to FIGS. 7-14, a method of assembling the implant 10 will be described. As shown in FIGS. 7 and 8, the distal tip 64 of the pivoting member 28 is aligned with a gap 74 in the track 70 along an axis A. The distal tip 64 may also be aligned with the pivoting dimple 72 along axis A. Turning to FIGS. 9 and 10, the pivoting member 28 is seated within the implant 10, but is not yet engaged with the track 70. The distal tip 64 or a portion thereof is received within the dimple 72 and the pivoting member 28 extends through the gap 74 and the head portion 60 of the pivoting member 28 protrudes slightly past the outer profile of the implant 10. Turning to FIGS. 11 and 12, the pivoting member 28 is articulated into a neutral position and into alignment with the track 70. When articulated into the neutral position, opening 76 is exposed to receive the blocking member 80.

Figure 13:
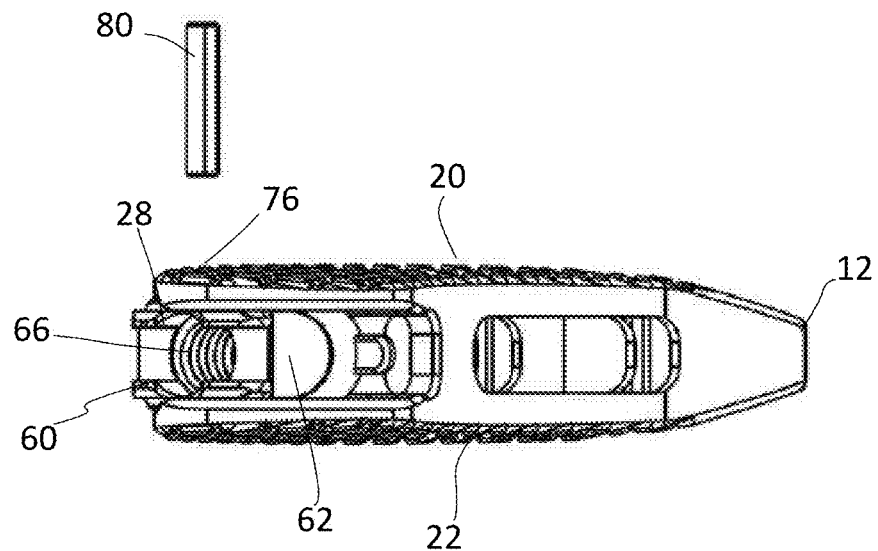
FIG. 13 is an exploded rear view of the implant with the porous portions omitted, housing the pivoting member, and a separate blocking component before the blocking component is installed.
Figure 14:
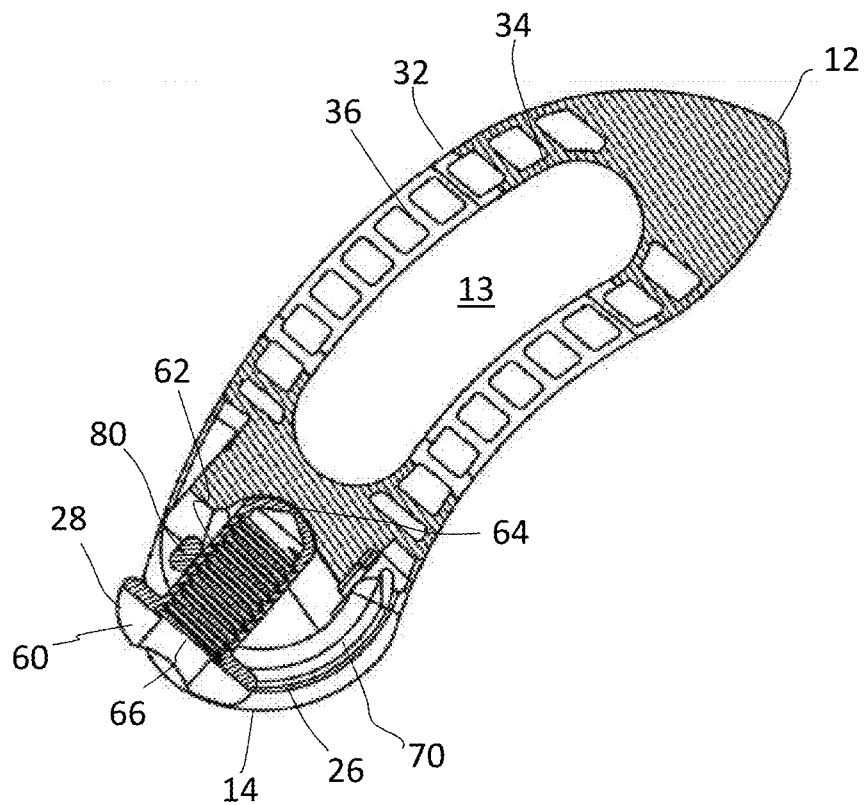
FIG. 14 is an assembled view of the implant with the porous portions omitted, the pivoting member, and the blocking component when the blocking component is fully installed.
Figure 19:
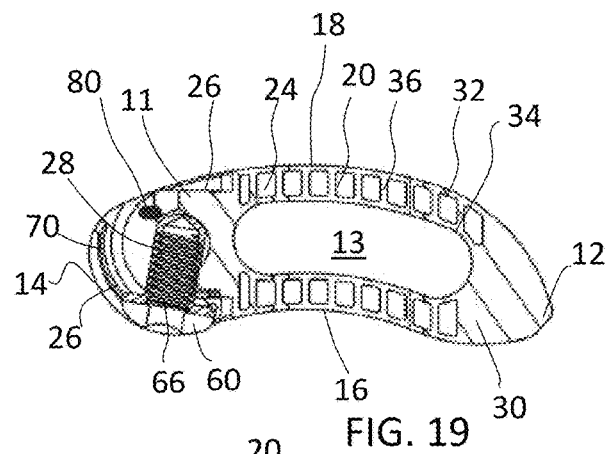
FIGS. 19 and 21 show the pivoting member articulated into the final implant position.

Turning to FIG. 13, the blocking member 80 is aligned with the opening 76. As shown in FIG. 14, the blocking member 80 is installed in the opening 76, thereby preventing the pivoting member 28 from pivoting back along the direction it was installed from. The blocking member 80 also prevents the pivoting member 28 from falling out of the opening 26. Once installed, the pivoting member 28 may articulate along the track or track 70 up to 75 degrees from the initial, horizontal position to the final, implanted position. The range of articulation may be limited by the track or tracks 70, the blocking member 80, and/or one or more stops built into the track 70 and/or opening 26. As best seen in FIG. 19, once the pivoting member 28 is articulated into its final position, the entire pivoting member 28 is housed entirely within opening 26 and is housed entirely within the spacer body 11. In other words, no portion of the pivoting member 28 protrudes beyond the outer profile of the implant 10. Because the pivoting member 28 is received completely within the opening 26, the pivoting member 28 does not contact the adjacent endplates of the vertebral bodies.

Figure 18:
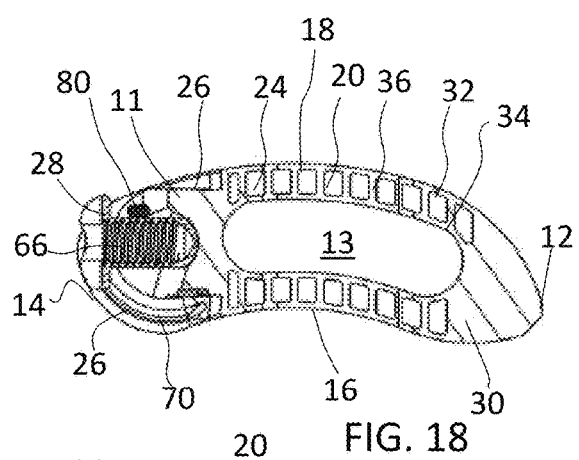
FIGS. 18 and 20 show the implant with the porous portions omitted and the pivoting member in an initial, insertion orientation.
Figure 20:
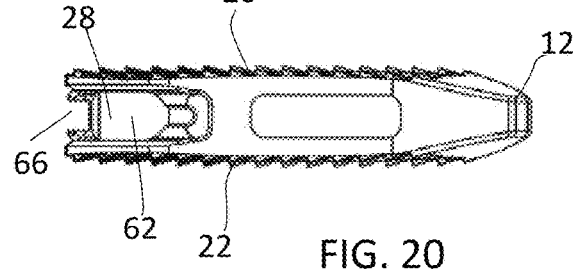
Figure 21:
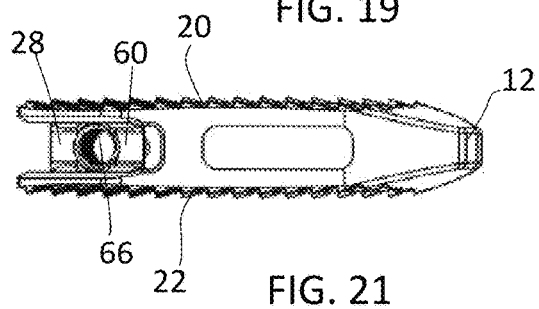

Turning now to FIGS. 18-21, a method of inserting and installing the articulating implant 10 will be described. As shown in FIGS. 18 and 20, the pivoting member 28 is in its initial, insertion position. An instrument (not shown) may be received within the instrument receiving recess 66 of the pivoting member 28. The implant 10 may be installed through a transforaminal approach, for example, although any suitable installation approach may be selected by the surgeon. Once between the vertebrae, the pivoting member 28 may be moved along track or tracks 70, in-situ, such that the implant body 11 pivots into its final, installed position within the disc space. Thus, the implant body 11 may pivot up to 75 degrees relative to its initial position. After the final positioning is achieved, the instrument may be removed. The ability to articulate the implant 10 in-situ allows the surgeon to safely navigate past the posterior neural elements and/or optimize the implant placement relative to the patient anatomy.

Figure 22:
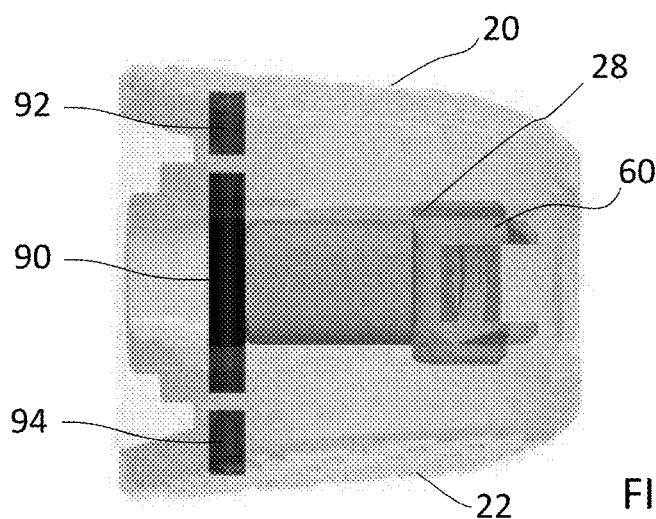
FIGS. 22-24 depict the implant with radiographic markers identifying the orientation of the implant within the disc space.
Figure 23:
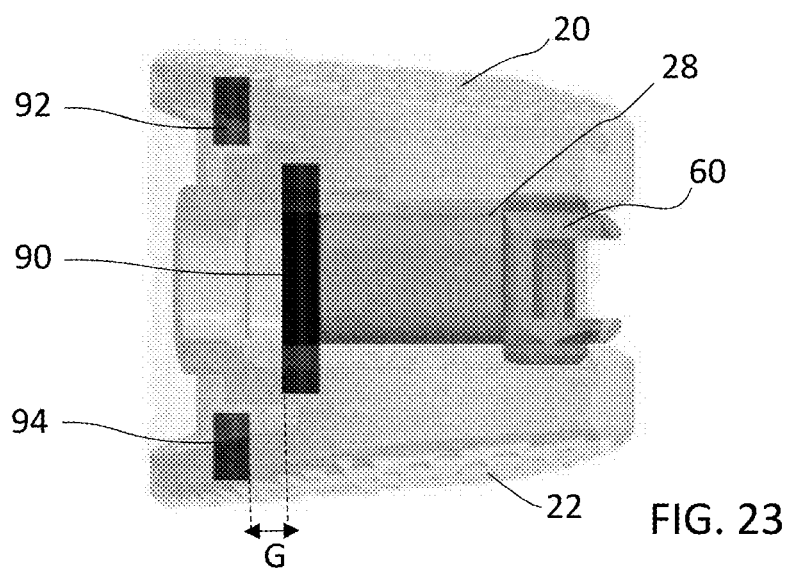
Figure 24:
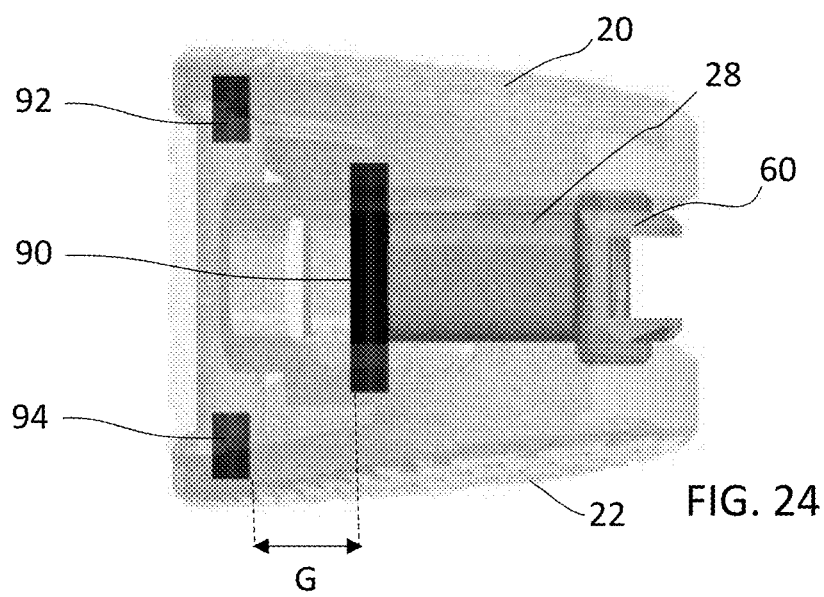

As shown in FIGS. 22-24, one or more radiographic markers 90, 92, 94 may be provided within the implant 10 in order to identify the orientation of the spacer within the disc space, for example, using X-ray or other imaging. As shown, a first radiographic marker 90 may be positioned centrally within the implant 10. The first marker 90 may be positioned, for example, near the distal end 64 of the pivoting member 28. A second radiographic marker 90 may be positioned near the upper surface 20, and a third radiographic marker 94 may be positioned near the lower surface 20 of the implant 10. The markers 90, 92, 94 may be generally cylindrical in shape. In addition, the second and third markers 92, 94 may be shorter in length than the first marker 90. Although this configuration is shown, it will be envisioned that any suitable location, spacing, shape, and size of the markers may be selected.

After the implant 10 has been articulated into position within the disc space, the proper positioning of the implant 10 can be ascertained, as best seen in FIG. 22, by generally coaxially aligning the first marker 90 with the second and third markers 92, 94 respectively. FIG. 23 depicts what a radiographic image would look like when the implant is about 5 degrees under-rotated, and FIG. 24 depicts a radiographic image when the implant 10 is about 10 degrees under-rotated. Thus, a surgeon observing no alignment between the markers 90, 92, 94 would know that the implant 10 was not fully articulated into its final position. Furthermore, one could ascertain by looking at the imaging that a larger gap G between the first marker 90 and the second and third markers 92, 94 (e.g., shown in FIG. 24) would represent that the implant 10 is further out of position than a smaller gap G between the first marker 90 and the second and third markers 92, 94 (e.g., shown in FIG. 23). In other words, the surgeon would know that the implant is moving in the correct direction as gap G becomes smaller and the markers 90, 92, 94 are ultimately aligned in the final implant position (shown in FIG. 22).

The implants of the disclosure may be manufactured from traditional manufacturing processes (machining) or those later developed. In one embodiment, the implants are made by additive manufacturing or 3D printing. Various forms of additive manufacturing, or 3D printing, have been developed which allow structures to be formed layer by layer. One illustrative 3D printing technology is Direct Metal Laser Sintering (DMLS) wherein parts are built using a laser to selectively sinter (heat and fuse) a powdered metal material into layers. The process begins once a 3D CAD file is mathematically sliced into multiple 2D cross sections and uploaded into the system. After the first layer is produced, the build platform is lowered, another powder layer is spread across the plate, and the laser sinters the second layer. This process is repeated until the part is complete. Layer-by-layer manufacturing allows for the direct fabrication of complex parts that would be cost-prohibitive, and often impossible, to produce through traditional manufacturing processes. The powder layer thickness used during the fabrication of the spacers may be as thin at 30 µm, for example. The resolution of the laser may be as fine as 70 µm, for example. Although it is envisioned that any suitable thickness or laser resolution may be used or selected.

The disclosure is not limited to DMLS, but various 3D printing methods may be utilized. For example, VAT photopolymerization utilizes a vat of liquid photopolymer resin which is cured through selective exposure to light (via a laser or projector) which then initiates polymerization and converts the exposed areas to a solid part. As another example, Powder Bed Fusion, of which DMLS is a subcategory, utilizes powdered materials which are selectively consolidated by melting it together using a heat source such as a laser or electron beam. The powder surrounding the consolidated part acts as support material for overhanging features. As yet another example, in Binder Jetting Liquid bonding agents are selectively applied onto thin layers of powdered material to build up parts layer by layer. The binders include organic and inorganic materials. Metal or ceramic powdered parts are typically fired in a furnace after they are printed. Material Jetting is another example of a 3D printing process which may be utilized wherein droplets of material are deposited layer by layer to make parts. Common varieties include jetting a photocurable resin and curing it with UV light, as well as jetting thermally molten materials that then solidify in ambient temperatures. As another example, in Sheet Lamination sheets of material are stacked and laminated together to form an object. The lamination method can be adhesives or chemical (paper/plastics), ultrasonic welding, or brazing (metals). Unneeded regions are cut out layer by layer and removed after the object is built. Another example of a 3D printing process that may be utilized is Material Extrusion wherein material is extruded through a nozzle or orifice in tracks or beads, which are then combined into multi-layer models. Common varieties include heated thermoplastic extrusion and syringe dispensing. Yet another example is Directed Energy Deposition wherein powder or wire is fed into a melt pool which has been generated on the surface of the part where it adheres to the underlying part or layers by using an energy source such as a laser or electron beam. Although these 3D printing techniques are exemplified, it will be appreciated that any suitable techniques may be selected to build the implant designs.

The implants may also be manufactured utilizing a combination of additive manufacturing processes and other manufacturing processes, for example, machining or laser etching. Additionally, the implants may be processed during and/or after manufacture utilizing various techniques, for example, abrasion, machining, polishing, or chemical treatment. The implants may be manufactured from various materials, such as biocompatible materials, including metals, polymers, ceramics or combinations thereof. Exemplary materials include Titanium (and Titanium alloys), Cobalt-Chrome, PEEK, and/or Stainless Steel, for example.

Turning to FIG. 1, a 3D printed implant 10 is shown having a solid support structure 30 (shown as light portions) and a porous structure 50 (shown as dark portions) formed integral therewith. The configuration of the solid structure 30 is selected to provide the implant sufficient structural integrity and mechanical stability while maximizing the area of porous structure 50 which facilitates better integration/incorporation with the adjacent bone. The configuration of the support structure 30 and the porous structure 50 may be selected, for example, to provide the implant with an adequate construct strength while maximizing the potential for bony in-growth and allowing for clear radiographic imaging.

As shown in FIG. 1, the solid structure 30 may form a frame or support structure for the porous structure 50. The solid structure 30 may include an outer wall portion 32 and an inner wall portion 34. One or more cross-struts 36 may be provided between the outer and inner wall portions 32, 34. The porous structure 50 may fill the gaps between the solid structure 30. The porous structure 50 may extend from the upper surface 20 to the lower surface 22 or through a portion thereof. The porous structure 50 may also fill lateral windows 52 between the outer wall portion 32 and the inner wall portion 34. Alternatively, the lateral windows 52 may remain empty. When present, the porous structure 50 within the lateral windows 52 may be in communication with the hollow interior chamber 13. It is envisioned that alternative arrangements of solid and porous portions 30, 50 may be utilized. Suitable solid and/or porous structures may include those identified in U.S. patent application Ser. No. 16/151,737, filed Oct. 4, 2018, which is incorporated by reference herein in its entirety for all purposes.

The porous structure 50 may have a randomized pattern of open pores or a repeating pattern of open pores. The porous structure 50 may have a suitable porosity (open volume). For example, the porous structure 50 may be greater than 50% open, greater than 60% open, greater than 70% open, or approximately 70% open, or approximately 75% open. The porous structure 50 may feature interconnected pores or open pores. The porous structure 50 may have pores, for example, ranging from approximately 100 μm-2 mm, approximately 100 μm-1 mm, approximately 200-900 μm, or approximately 300-800 μm in diameter. The pore size may have an average pore size of about 300-800 μm, about 400-700 μm, or about 500-600 μm. The pore size distribution may be unimodal or bi-modal. Although spherical or partially-spherical pores or nodes are exemplified in forming the porous structure, it is envisioned that other suitable pore shapes and configurations may be used, for example, repeating or random patterns of cylinders, cubes, cones, pyramids, polyhedrons, or the like.

It is contemplated that different areas of the support structure 30 may have varying stiffness or strength, for example, variable A-P stiffness to achieve optimized load on an anterior graft or to achieve a desired level of flexibility within the implant 10. Furthermore, the porous structure 50 may have different porosities or densities in different areas of the implant 10. For example, the porous structure 50 may have a higher porosity or density along the inner perimeter compared to that at the outer perimeter, for example, with the inner area having a cancellous porosity and the outer area having a cortical porosity. The porous structure 50 may have various configurations, for example, a grid or honeycomb pattern which may promote bony in-growth. The surface texture of both the support structure and the porous structure may be controlled to provide both macro and micro texturizing. The features and characteristics described with respect to this embodiment may be incorporated in any of the embodiments described herein. Additionally, features described in any of the embodiments herein may be incorporated into any of the other embodiments.

With regard to the radiographic markers 90, 92, 94, these may also be formed during the 3D printing process or may be added, for example, as inserts after manufacturing. When created during the 3D printing process, it may be desirable to use different porosities to highlight certain areas of the implant for radiographic or other imaging. For example, it may be desirable that the markers 90, 92, 94 are more radiolucent and other portions of the implant are generally more radioopaque. The visualization of the marker 90, 92, 94 may be achieved, for example, by selecting which regions are porous and/or the degree of porosity during the 3D printing process.

Figure 15:
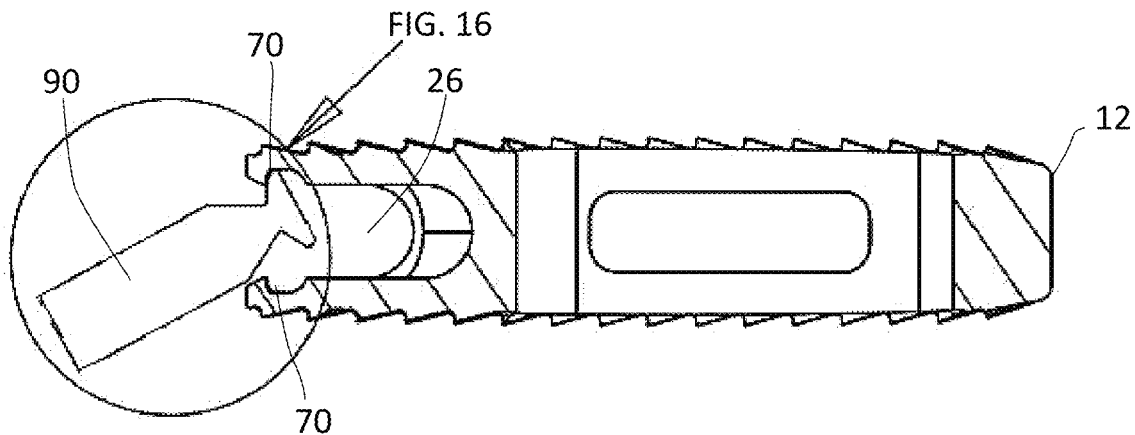
FIG. 15 shows a side view of the implant with the porous portions omitted with a cutter suitable to finish the track features.
Figure 16:
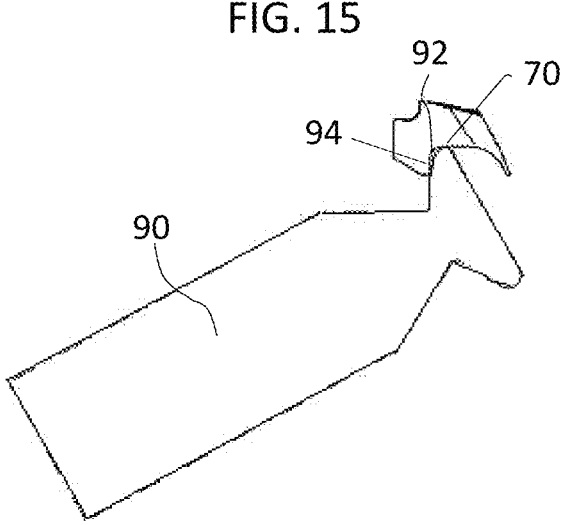
FIG. 16 is a close-up view of the cutter and track.
Figure 17:
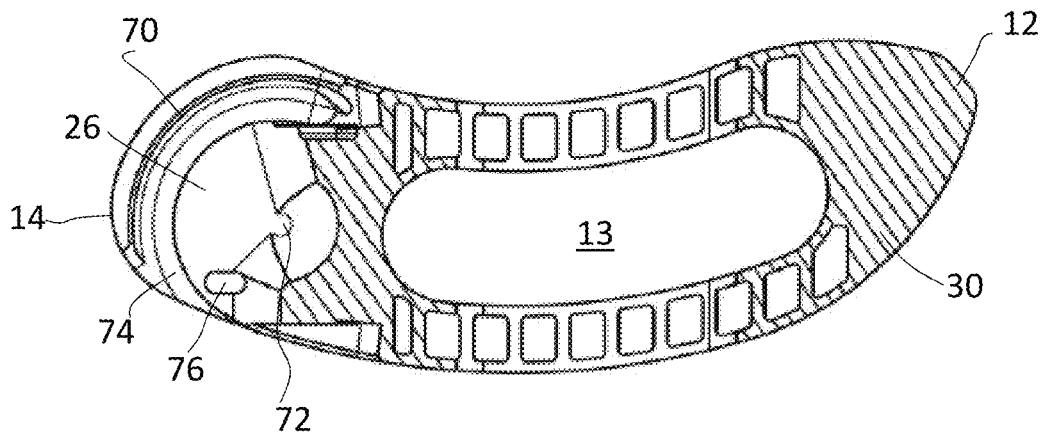
FIG. 17 is a cross-sectional view of the implant with the porous portions omitted.

Turning to FIGS. 15-16, a method of making and/or finishing the implant 10 will be described. The implant 10 may be constructed using a Direct Metal Laser Sintering process, such that each layer is added until the implant 10 is created. The tracks 70 may be created by traditional manufacturing processes or may be created by additive techniques and then refined for improved surface finish by subtractive processing. To refine the surface finish in this region, a dovetail cutter 90 may be employed as shown. In particular, a dovetail cutter 90 may have a curved cutting surface 92 configured to form a smooth vertical region 94 for track 70. The dovetail cutter 90 may generate the smooth vertical region 94, swept about the radius of the pivot arc. In other words, the dovetail cutter 90 may be moved about the curved radius of the track 70 to maintain the features of the female track 70. The dovetail cutter 90 may avoid the runout of other cutters which may distort the vertical region 94. Thus, the implant features may be finished to ensure tight tolerances and smooth surfaces, for example, for improved performance of the pivoting member 28.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. An intervertebral implant for implantation in an intervertebral space between vertebrae, the implant comprising:
   an implant body extending from an upper surface to a lower surface, the implant body having a front end, a rear end and a pair of spaced apart first and second side walls extending between the front and rear ends such that an interior chamber is defined within, wherein the rear end includes an elongated opening defining at least one track and a dimple, wherein the implant body is formed as a monolith;
   a pivoting member including an enlarged head portion and an elongated shaft portion terminating at a distal end, wherein the distal end is positioned within the dimple and the enlarged head portion is positioned within the at least one track; and
   a blocking member extending from the upper surface to the lower surface of the implant body and securing the pivoting member within the at least one track,
   wherein the blocking member extends through an opening in at least one of the upper surface and the lower surface,
   wherein the pivoting member is configured to slide along the at least one track and articulate from an initial position to a final position, and
   wherein in the final position, the pivoting member does not protrude past an outer footprint of the implant body.

2. The intervertebral implant of claim 1, wherein the at least one track includes an upper track and a lower track.

3. The intervertebral implant of claim 2, wherein an upper portion of the enlarged head portion is received within the upper track and a lower portion of the enlarged head portion is received within the lower track.

4. The intervertebral implant of claim 1, wherein the dimple acts as a pivot point for the pivoting member.

5. The intervertebral implant of claim 4, wherein the at least one track extends along an arc having a constant radius from the pivot point.

6. The intervertebral implant of claim 1, wherein a gap in the at least one track allows for the pivoting member to be inserted into the elongated opening.

7. The intervertebral implant of claim 1, wherein the pivoting member includes an instrument receiving recess extending into the shaft portion, thereby forming a blind hole.

8. The intervertebral implant of claim 7, wherein the instrument receiving recess extending into the shaft portion is internally threaded.

9. The intervertebral implant of claim 1, wherein the implant body includes a solid support structure and an integral porous structure.

10. The intervertebral implant of claim 9, wherein the integral porous structure is disposed in vertical walls of the implant and are formed of additively 3-D printed structure.

11. The intervertebral implant of claim 9, wherein:
    the integral porous structure is disposed in vertical walls and are formed of additively 3-D printed structure; and
    the integral porous structure includes interconnected pores having an average pore size of between 300-800 μm.

12. An intervertebral implant for implantation in an intervertebral space between vertebrae, the implant comprising:
    an implant body extending from an upper surface to a lower surface, the implant body having a front end, a rear end and a pair of spaced apart first and second side walls extending between the front and rear ends such that an interior chamber is defined within, wherein the rear end includes an elongated opening defining an upper track, a lower track, and a dimple, wherein the implant body is formed as a monolith;
    a pivoting member including an enlarged head portion and an elongated shaft portion terminating at a distal end, wherein the distal end is positioned within the dimple and the enlarged head portion is positioned within the upper and lower tracks; and
    a blocking member extending from the upper surface to the lower surface of the implant body and securing the pivoting member within the upper and lower tracks,
    wherein the blocking member extends through an opening in at least one of the upper surface and the lower surface,
    wherein the pivoting member is configured to slide along the upper and lower tracks and articulate from an initial position to a final position; and
    wherein in the final position, the pivoting member does not protrude past an outer footprint of the implant body.

13. The intervertebral implant of claim 12, wherein an upper portion of the enlarged head portion is received within the upper track and a lower portion of the enlarged head portion is received within the lower track.

14. The intervertebral implant of claim 12, wherein the dimple acts as a pivot point for the pivoting member.

15. The intervertebral implant of claim 14, wherein the upper and lower tracks each extend along an arc having a constant radius from the pivot point.

16. The intervertebral implant of claim 12, wherein a gap in each of the upper and lower tracks allows for the pivoting member to be inserted into the elongated opening.

17. The intervertebral implant of claim 12, wherein the pivoting member includes an instrument receiving recess extending into the shaft portion, thereby forming a blind hole.

18. The intervertebral implant of claim 17, wherein the instrument receiving recess extending into the shaft portion is internally threaded.

19. The intervertebral implant of claim 12, wherein the implant includes a solid support structure and an integral porous structure.

20. The intervertebral implant of claim 12, wherein the implant body includes three radiographic markers, and the implant is in the final position when the three radiographic markers are aligned along a common axis.

* * * * *